United States Patent
Adachi et al.

(10) Patent No.: US 8,852,511 B2
(45) Date of Patent: Oct. 7, 2014

(54) AUTOMATIC ANALYZER

(75) Inventors: Sakuichiro Adachi, Hitachinaka (JP); Muneo Maeshima, Mito (JP); Isao Yamazaki, Ryugasaki (JP); Tomonori Mimura, Kasama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 288 days.

(21) Appl. No.: 13/382,316

(22) PCT Filed: Jul. 5, 2010

(86) PCT No.: PCT/JP2010/061369
§ 371 (c)(1),
(2), (4) Date: Feb. 1, 2012

(87) PCT Pub. No.: WO2011/004781
PCT Pub. Date: Jan. 13, 2011

(65) Prior Publication Data
US 2012/0141330 A1  Jun. 7, 2012

(30) Foreign Application Priority Data

Jul. 10, 2009  (JP) ................................. 2009-163987

(51) Int. Cl.
G01N 33/00   (2006.01)
G01N 21/51   (2006.01)

(52) U.S. Cl.
CPC ...................................... G01N 21/51 (2013.01)
USPC .......... 422/82.05; 422/68.1; 422/50; 422/500

(58) Field of Classification Search
USPC ................................ 422/68.1, 82.05, 50, 500
See application file for complete search history.

(56) References Cited

U.S. PATENT DOCUMENTS

| 4,451,433 A | 5/1984 | Yamashita et al. |
| 6,791,676 B1 | 9/2004 | Meller |
| 2004/0012782 A1 | 1/2004 | Mason et al. |

FOREIGN PATENT DOCUMENTS

| JP | 1-295134 | 11/1989 |
| JP | 5-45282 | 2/1993 |
| JP | 5-72210 | 3/1993 |
| JP | 10-332582 | 12/1998 |
| JP | 2000-65744 | 3/2000 |
| JP | 2001-141654 | 5/2001 |
| JP | 2005-536721 | 12/2005 |
| JP | 2008-8794 | 1/2008 |

OTHER PUBLICATIONS

V.V. Teselkin, Application Limits of Laser Radiation Small Angle Dispersion for Dispersion Analysis of Water Suspensions, ISSN: 0204-35561, 1985, pp. 82-84, vol. 7, No. 1.

*Primary Examiner* — Sam P Siefke
(74) *Attorney, Agent, or Firm* — Antonelli, Terry, Stout & Kraus, LLP.

(57) ABSTRACT

To be adapted to various types of latex reagents for detecting scattered light and thereby measuring agglutination reactions with high sensitivity while sufficiently ensuring integration time. To be adapted to various types of latex particles of different particle sizes, a plurality of light receivers are arranged in a plane perpendicular to the direction of cell movement by rotation of a cell disk. To ensure sufficient integration time, the angle between the optical axis of the irradiation light and each of a plurality of optical axes of scattered light viewed from above the cell is made equal to or less than 17.7° including a mounting error.

8 Claims, 10 Drawing Sheets

AUTOMATIC ANALYZER

TECHNICAL FIELD

The present invention relates to a sample analyzer that analyzes a sample to determine the amount of constituent contained therein, and for example, an automatic analyzer that analyzes blood or urine to determine the amount of constituent contained therein.

BACKGROUND ART

As a sample analyzer for analyzing a sample to determine the amount of constituent contained therein, there has been widely used an automatic analyzer that emits light from a light source to a sample or a reaction mixture of a sample and a reagent; measures the amount of transmitted light of a single or a plurality of wavelengths obtained therefrom to calculate the absorbance; and determines the amount of constituent from the relation between the absorbance and the concentration according to the Beer-Lambert law (for example, see Patent Literature 1). The analyzer has a cell disk that repeats rotation and termination and a large number of cells holding a reaction mixture are arranged circumferentially thereon. During the cell disk rotation, a preset transmitted light measuring unit measures the change in absorbance over time for about ten minutes at a specific time interval.

The automatic analyzer includes a system for measuring the amount of transmitted light. The reaction of a reaction mixture is roughly divided into two types: an enzyme-substrate color reaction and an antigen-antibody agglutination reaction. The former is a biochemical analysis and includes LDH (lactate dehydrogenase), ALP (alkaline phosphatase), AST (aspartate aminotransferase), and the like as the test items. The latter is an immunoassay and includes CRP (C-reactive protein), IgG (immunoglobulin), RF (rheumatoid factor), and the like as the test items. The analyte to be measured by the latter immunoassay has a low blood level, and hence high sensitivity is required. Conventionally, high sensitivity has been provided by an immunological latex agglutination in such a manner that a reagent with an antibody sensitized (bound) to a latex particle surface is used; when a constituent contained in a sample is recognized and agglutinated, light is emitted to a reaction mixture; and then the mount of constituent contained in the sample is quantified by measuring the amount of light transmitted but not scattered by the latex aggregate.

Further, as the analyzer, an attempt has been made to increase sensitivity not by measuring the amount of transmitted light but by measuring the amount of scattered light. For example, there are disclosed a system that uses a diaphragm to separate the transmitted light and the scattered light and measure the absorbance and the scattered light at the same time (Patent Literature 2); a configuration in which precision is increased on a high concentration side by measuring the scattered light reflected by a large aggregate formed as a result of advanced agglutination reaction (Patent Literature 3); a method in which in front of and at the back of a reactor vessel, an integrating sphere is used to measure an average amount of light of each of the forward scattered light and the backward scattered light and correct turbidity changes due to cell dislocation (Patent Literature 4); a method of facilitating reduction in size and adjustment of the analyzer by arranging a fluorescent light-scattered light measurement detection system on the same plane as the direction of cell rotation (Patent Literature 5), and the like.

CITATION LIST

Patent Literature

Patent Literature 1: U.S. Pat. No. 4,451,433
Patent Literature 2: JP 2001-141654 A
Patent Literature 3: JP 2008-8794 A
Patent Literature 4: JP 10-332582 A
Patent Literature 5: JP 1-295134 A

SUMMARY OF INVENTION

Technical Problem

The amount of scattered light greatly changes according to the wavelength of irradiation light, the particle size of a particle as the scatterer, and the scattering angle. Accordingly, in order to obtain high sensitivity, it is important to detect the scattered light using the scattered light receiving angle according to the particle size of a latex reagent. Various types of latex reagents are used in an automatic analyzer as a general-purpose apparatus. The particle size of the latex particle is generally about 0.1 µm to 1.0 µm, but the particle size is not disclosed. According to conventional techniques, even an automatic analyzer configured to detect scattered light cannot handle latex reagents of various particle sizes. Thus, the arrangement capable of detecting a latex reagent of any particle size with high sensitivity is not clarified.

Further, in recent years, in order to reduce reagent running costs, reduction in cell size is progressing by reducing the amount of reaction mixture, resulting in the reduction in cell size with an optical path length of about 5 mm and a cell width of about 2.5 mm. Particularly, the cell width is shrinking. However, the measurement of the change in absorbance over time requires data in a shorter time interval, and hence the cell rotation speed cannot be reduced. Therefore, the integration time for each measurement is shortened. When the automatic analyzer measures the scattered light, the automatic analyzer needs to measure the rotating cells. Particularly the amount of scattered light is smaller than that of transmitted light, and hence it is important to secure the integration time.

Patent Literature 2 discloses a configuration capable of measuring the scattered light and the transmitted light at the same time, but does not reveal the configuration of arranging a scattered light receiver according to various types of latex particle sizes. Patent Literature 2 uses a diaphragm to obtain the scattered light around the entire circumference, but does not consider the cell width or the integration time.

Patent Literature 3 obtains the scattered light for the purpose of increasing the precision on the high concentration side, but is not effective for increasing sensitivity on the low concentration side.

Patent Literature 4 uses an integrating sphere to average the scattered light, but is not effective for increasing sensitivity. In addition, Patent Literature 4 is a system for measuring the scattered light while the cell is not rotating, and does not consider the cell width or the integration time for a general-purpose automatic analyzer to measure the scattered light while the cell is rotating.

Patent Literature 5 limits the scattered light measuring direction to 90°, and hence does not clarify whether to increase sensitivity according to various types of latex particle sizes.

Thus, the above disclosed techniques do not clarify a specific configuration capable of increasing sensitivity according to various types of latex reagents and increasing sensitivity for scattered light measurement while securing the integration time.

Solution to Problem

The present invention provides a configuration of arranging a plurality of light receivers in a forward direction in a plane perpendicular to the direction of cell rotation so as to increase sensitivity according to each of various types of latex particle sizes.

The automatic analyzer of the present invention includes a cell disk that holds a cell containing a reaction mixture of a sample and a reagent on a circumference thereof and repeats rotation and termination; and a scattered light measuring unit including a light source and a light receiver, that irradiates the cell with irradiation light from the light source during rotation of the cell disk and measures the scattered light due to the reaction mixture in the cell. The scattered light measuring unit includes a plurality of light receivers arranged in a plane perpendicular to the direction of cell movement due to the rotation of the cell disk and receiving scattered light of each of different scattering angles. From the point of view of sufficiently securing the integration time at scattered light measurement, the angle between the optical axis of the irradiation light and the optical axis of scattered light received by each light receiver viewed from a direction perpendicular to a rotating plane of the cell disk is preferably set to ±17.7° or less.

Preferably one of the plurality of light receivers is arranged at a position for receiving scattered light with a scattering angle close to the transmitted light axis, and the other one is arranged at a position for receiving scattered light between a first dark ring and a first bright ring. For example, the first light receiver is arranged at a position for receiving scattered light with a scattering angle of 30° or less, and the second light receiver is arranged at a position for receiving the scattered light with at least part of the scattering angles among the scattering angles of 30° to 50°.

Advantageous Effects of Invention

The automatic analyzer according to the present invention can receive scattered light at a plurality of angles while securing the integration time. Thus, the automatic analyzer can measure various types of latex reagents with high sensitivity. Thus, the automatic analyzer can achieve increased sensitivity and precision for the conventional test items and can be expected to handle new test items. Further, a diluted sample can be used for detection, and hence the amount of samples can be reduced.

DESCRIPTION OF EMBODIMENTS

FIGS. 1 to 9 illustrate the results of calculation of an angular dependence of the scattered light intensity when one latex particle (particle size from 0.1 µm to 1.0 µm) in the water is irradiated with light and an angular dependence of the ratio of change in the scattered light intensity when the particle size of a latex particle changes by 1% considering low concentration for high sensitivity measurement and assuming a case in which a small amount of constituent is contained in the sample and only a few constituent agglutinates.

Here, the change ratio in the description is defined as a value after change divided by a value before change. Specifically, when there is no change, the change ratio is calculated as 1. The light amount change (%) is defined as a value (a value after change−a value before change) divided by the value before change. Specifically, when there is no change, the light amount change (%) is calculated as 0. These values are useful as a simple approximation. The wavelength of irradiation light is set to 570 nm that has been used for conventional measurement of transmitted light. When measured, the scattered light scattered in a reaction mixture and transmitted through a glass window is measured in the air, and hence these effects are approximated and considered in the measurement. The above calculation is based on the discussion and calculation in a wide range of the scattered light theories. One example of the scattered light theories is described by C. F. Bohren and D. R. Huffman: Absorption and Scattering of Light by Small Particles, J. Wiley & Sons, 1983.

Figure 1:
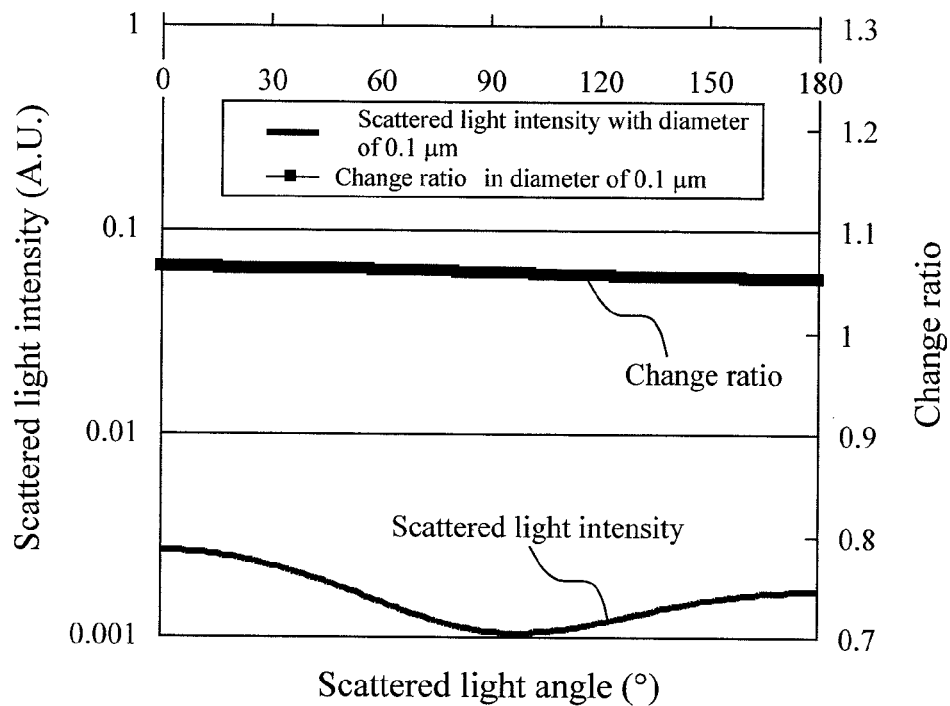
FIG. 1 is a graph illustrating an angular dependence of the scattered light intensity for a particle with a particle size of 0.1 µm and an angular dependence of the ratio of change when the particle size changes by 1%.
Figure 2:
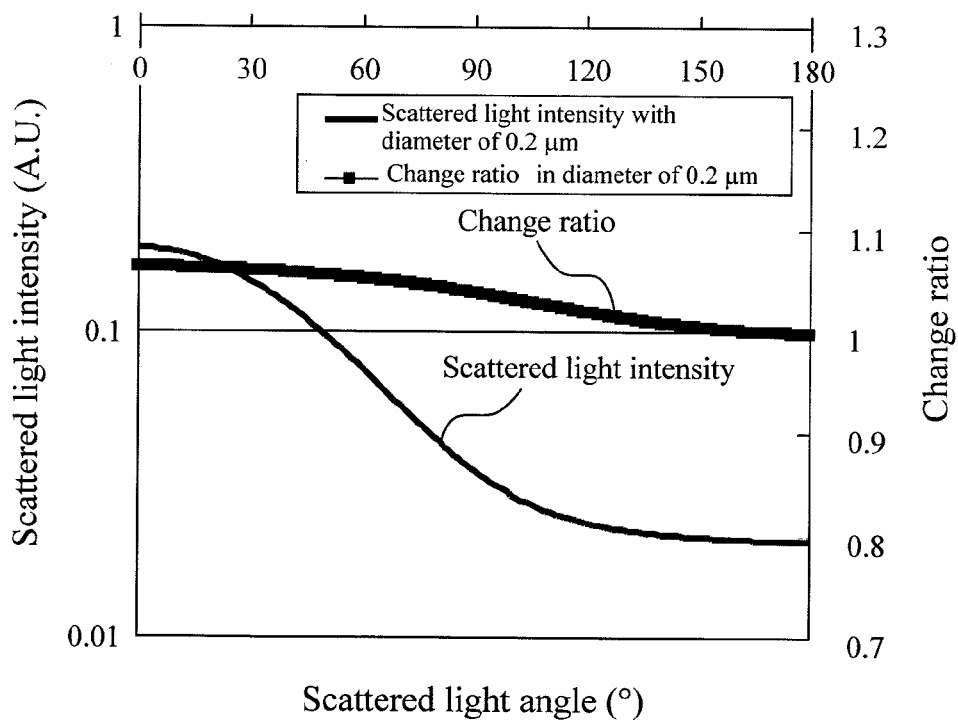
FIG. 2 is a graph illustrating an angular dependence of the scattered light intensity for a particle with a particle size of 0.2 µm and an angular dependence of the ratio of change when the particle size changes by 1%.
Figure 3:
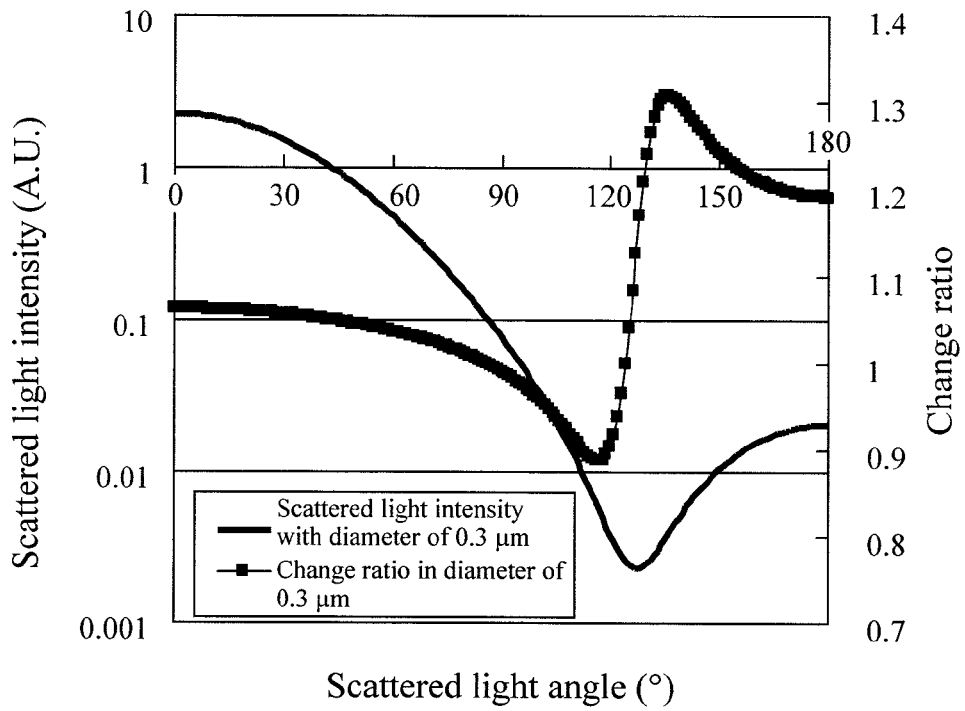
FIG. 3 is a graph illustrating an angular dependence of the scattered light intensity for a particle with a particle size of 0.3 µm and an angular dependence of the ratio of change when the particle size changes by 1%.
Figure 4:
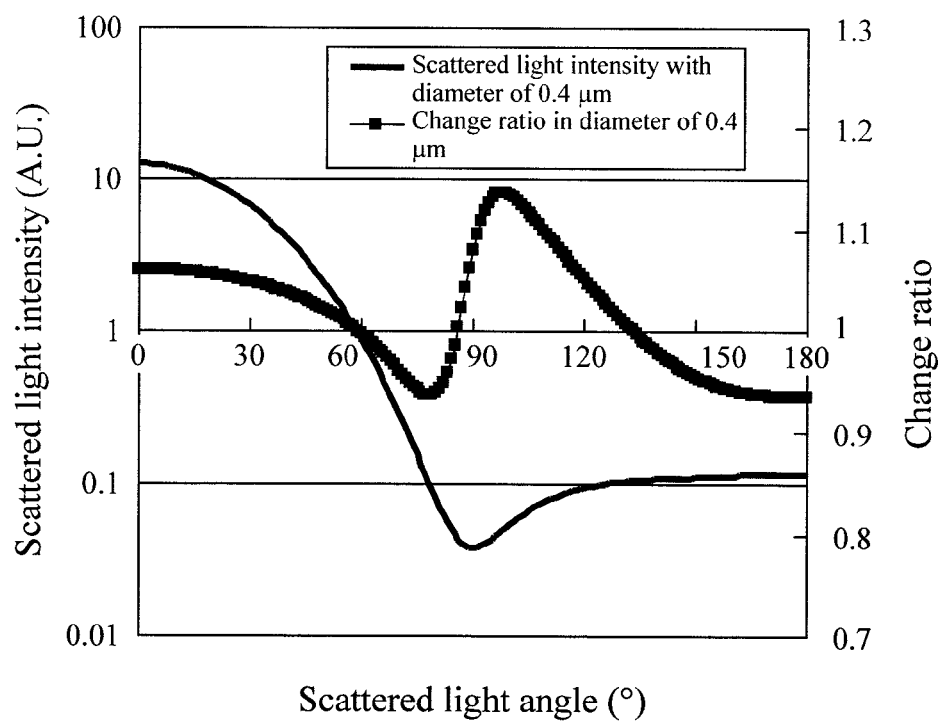
FIG. 4 is a graph illustrating an angular dependence of the scattered light intensity for a particle with a particle size of 0.4 µm and an angular dependence of the ratio of change when the particle size changes by 1%.
Figure 5:
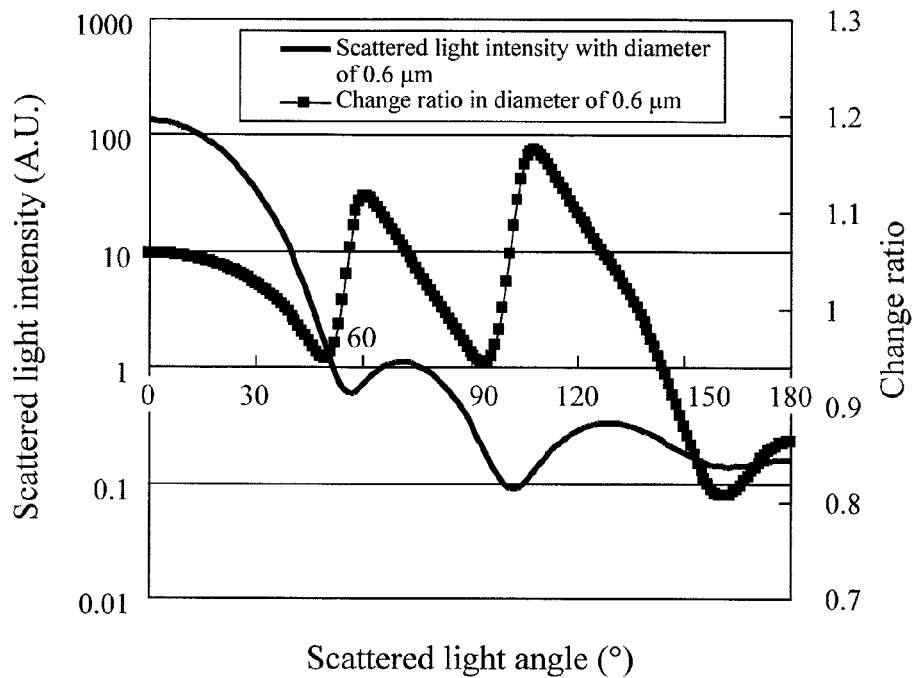
FIG. 5 is a graph illustrating an angular dependence of the scattered light intensity for a particle with a particle size of 0.6 µm and an angular dependence of the ratio of change when the particle size changes by 1%.
Figure 6:
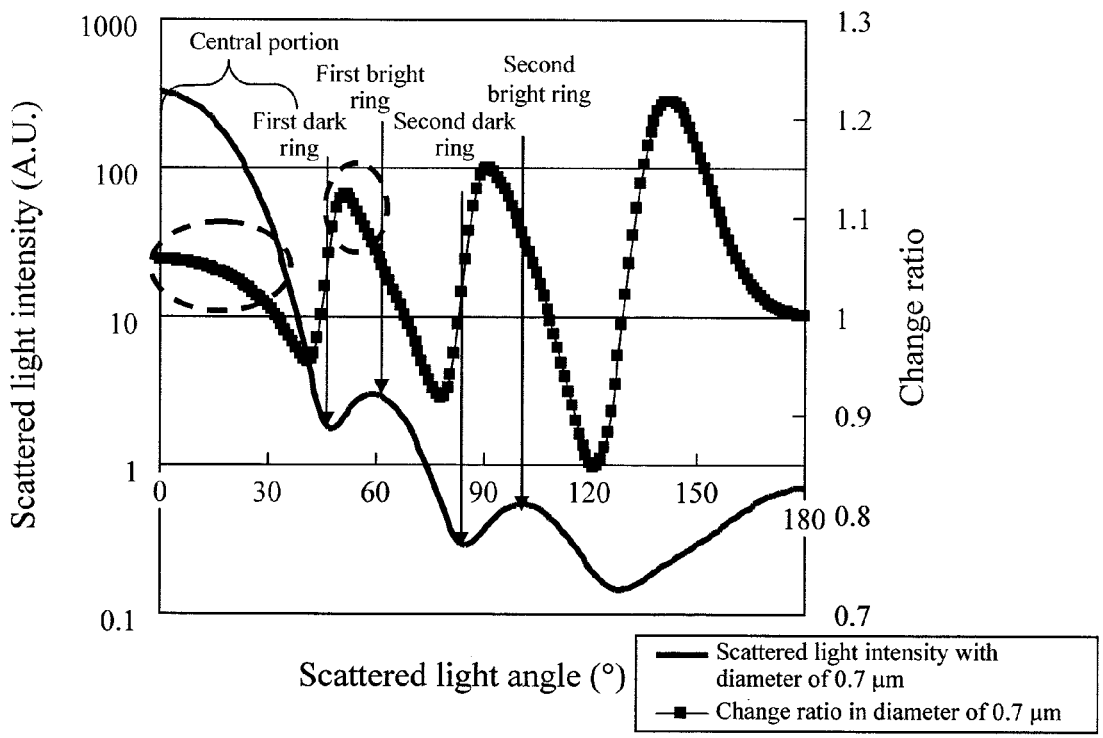
FIG. 6 is a graph illustrating an angular dependence of the scattered light intensity for a particle with a particle size of 0.7 µm and an angular dependence of the ratio of change when the particle size changes by 1%.
Figure 7:
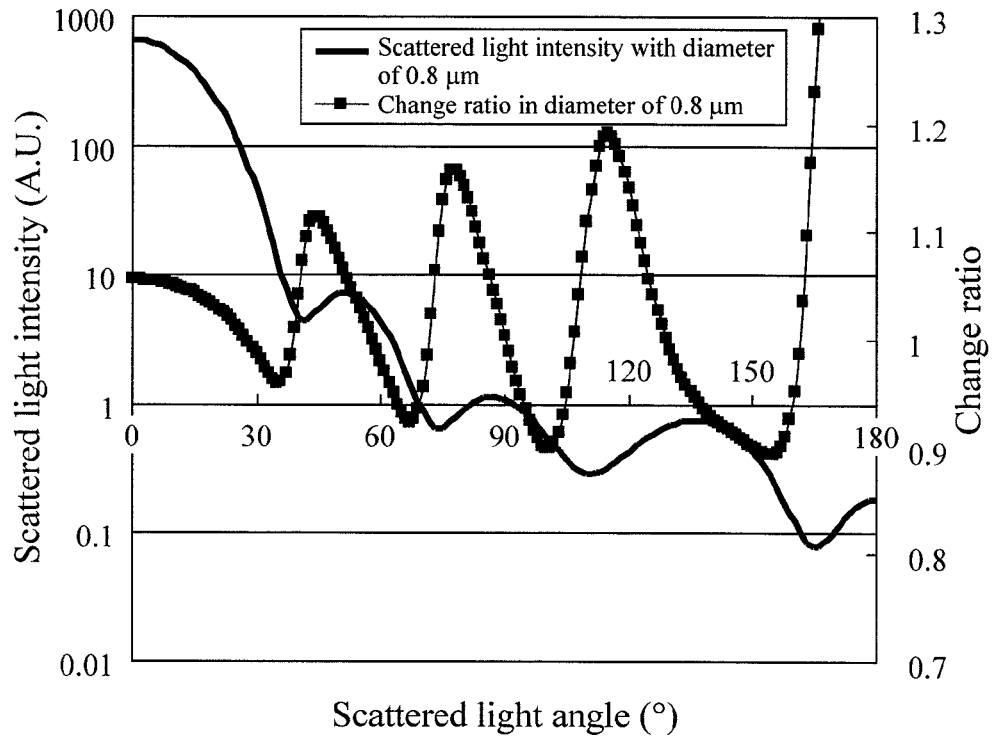
FIG. 7 is a graph illustrating an angular dependence of the scattered light intensity for a particle with a particle size of 0.8 µm and an angular dependence of the ratio of change when the particle size changes by 1%.
Figure 8:
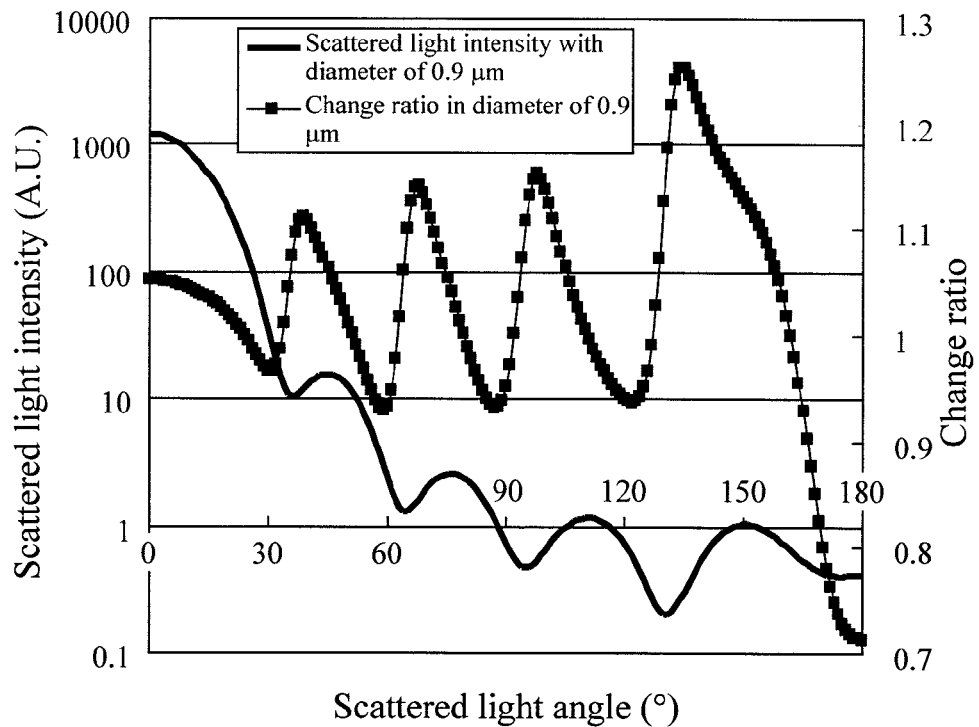
FIG. 8 is a graph illustrating an angular dependence of the scattered light intensity for a particle with a particle size of 0.9 µm and an angular dependence of the ratio of change when the particle size changes by 1%.
Figure 9:
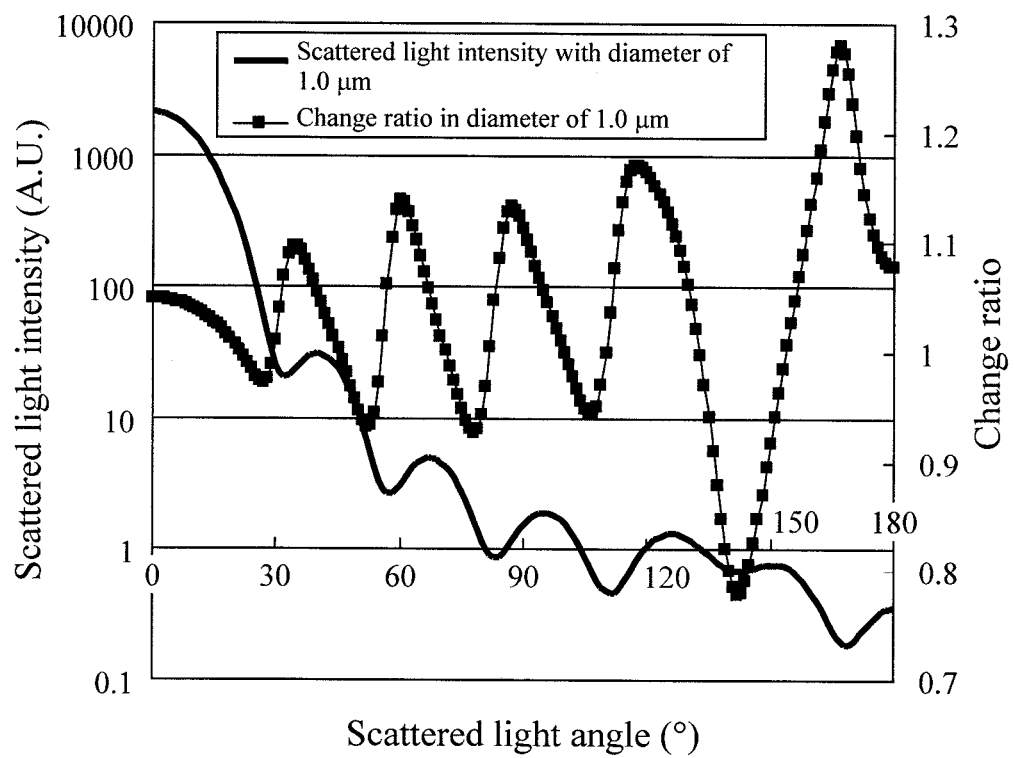
FIG. 9 is a graph illustrating an angular dependence of the scattered light intensity for a particle with a particle size of 1.0 µm and an angular dependence of the ratio of change when the particle size changes by 1%.

FIG. 1 is a graph of a latex particle with a particle size of 0.1 µm; FIG. 2 is a graph of a latex particle with a particle size of 0.2 µm; FIG. 3 is a graph of a latex particle with a particle size of 0.3 µm; FIG. 4 is a graph of a latex particle with a particle size of 0.4 µm; FIG. 5 is a graph of a latex particle with a particle size of 0.6 µm; FIG. 6 is a graph of a latex particle with a particle size of 0.7 µm; FIG. 7 is a graph of a latex particle with a particle size of 0.8 µm; FIG. 8 is a graph of a latex particle with a particle size of 0.9 µm; and FIG. 9 is a graph of a latex particle with a particle size of 1.0 µm.

As illustrated by the graph in FIG. 6, the scattered light intensity has several peaks depending on the scattering angle. The range of scattering angles from a scattering angle of 0° up to an angle of a first downward convex peak of the scattered light intensity is defined as a central portion; an angle of a upward convex peak of the scattered light intensity in the range in which the scattering angle is larger than that of the central portion is defined as a bright ring; and an angle of a downward convex peak thereof is defined as a dark ring, which are numbered sequentially from the central portion. More specifically, the number starts from the scattering angle of 0° followed by the central portion, a first dark ring, a first bright ring, a second dark ring, a second bright ring, and so on. These positions can be calculated from the wavelength of irradiation light, the size of a particle, the refractive index of the particle, and the refractive index of the medium. It is understood from FIG. 6 that the regions of a large scattering angle in the direction in which the change ratio of the scattered light intensity increases when the particle size changes by 1% are located in a central portion with an angle close to 0°, or between the dark ring and the following bright ring such as between the first dark ring and the first bright ring and between the second dark ring and the second bright ring. The scattering light can be measured with high sensitivity by arranging a light receiver at each position in which the change ratio increases for measurement.

Further, measurement can be made with high sensitivity by arranging the light receiver at a position in which the change ratio decreases. Furthermore, measurement can also be made with high sensitivity in a region of a scattering angle having a large amount of reduction in a direction in which the change ratio decreases such as by being located between the central portion and the dark ring or between the bright ring and the following dark ring such as before the first dark ring or between the first bright ring and the second dark ring. Thus, the accuracy can be further increased by arranging a large number of light receivers in such a region and by measuring the increase or decrease in the change ratio. Accordingly, it is useful to arrange a large number of light receivers.

Figure 10:
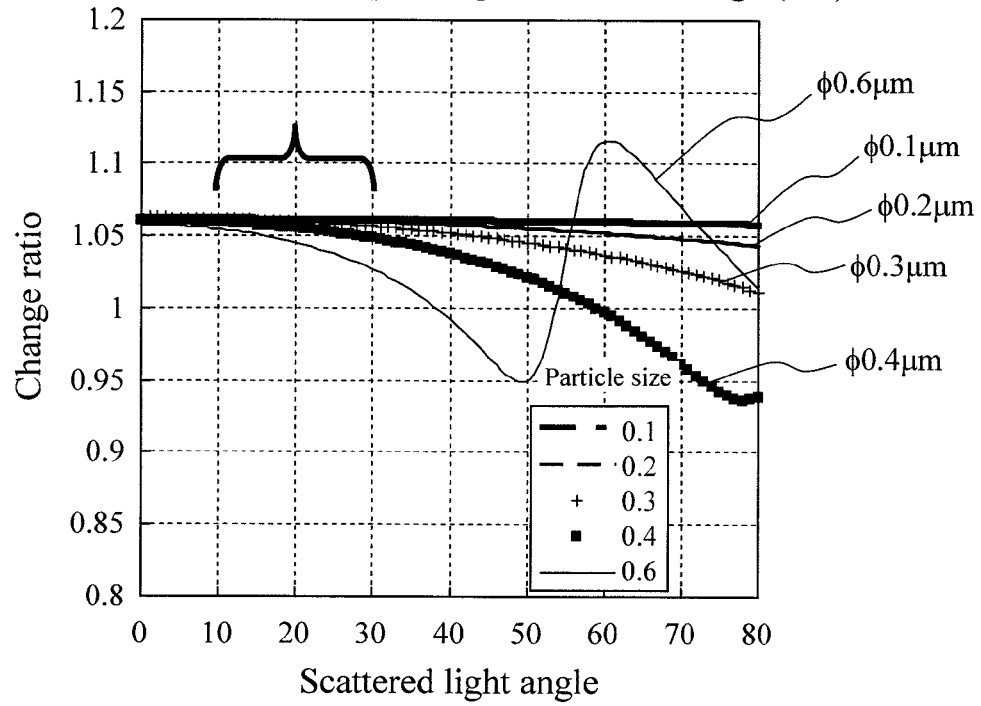
FIG. 10 is a graph illustrating an angular dependence of the scattered light intensity change ratio of a particle with a particle size of 0.1 µm to 0.6 µm with respect to a particle size change of 1%.
Figure 11:
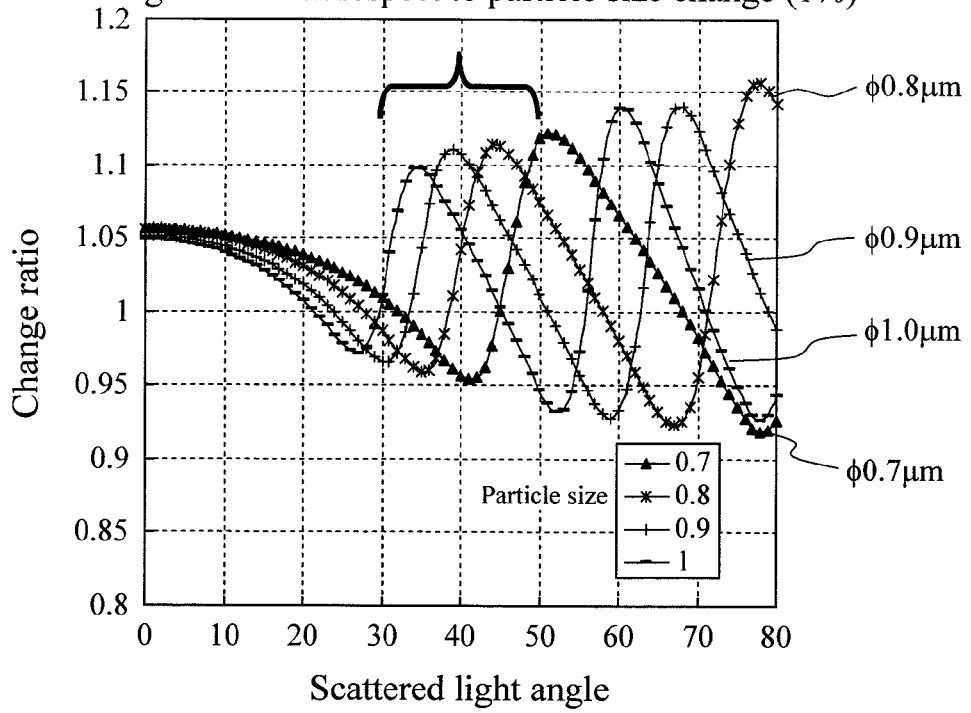
FIG. 11 is a graph illustrating an angular dependence of the scattered light intensity for a particle with a particle size of 0.7 µm to 1.0 µm with respect to the ratio of change in particle size by 1%.

Next, FIG. 10 collectively illustrates the change ratios for particles with a particle size of 0.1 µm to 0.6 µm; and FIG. 11 collectively illustrates the change ratios for particles with a particle size of 0.7 µm to 1.0 µm. It is understood from FIG. 10 that for the particles with a particle size of 0.1 µm to 0.6 µm, the central portion with an angle near 20°±10° is advantageous for increasing the sensitivity at measurement, considering that the region close to an angle of 0° is not suitable for receiving scattered light because of incident irradiation light. In contrast to this, it is understood from FIG. 11 that for the particles with a particle size of 0.7 µm to 1.0 µm, the change ratio decreases in the central portion with an angle of 20°±10°, and hence the region with a scattering angle near 40°±10° in which a light receiver is located between the first dark ring and the first bright ring is advantageous for measuring the particles of such a particle size with high sensitivity. Thus, in order to handle the reagents of various particle sizes, scattered light detectors are desirably arranged in a plurality of positions in the central portion and between the first dark ring and the first bright ring. More specifically, measurement can be made with high sensitivity for any reagent of various reagent particle sizes by arranging an optical system such that the light receiving angle becomes a plurality of angles equal to or less than 30° and equal to or greater than 30°.

Figure 12:
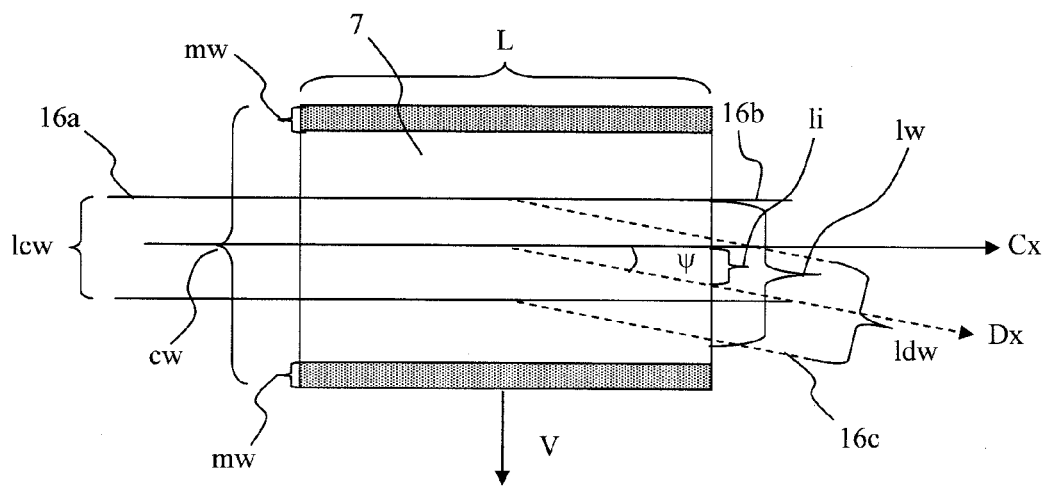
FIG. 12 is an explanatory drawing of integration time estimation.

Next, referring to FIG. 12, the scattered light receiving angle and the integration time will be described. FIG. 12 illustrates a cell viewed from above, namely, from the direction perpendicular to a rotating plane of a cell disk holding the cell and rotating (will be described later referring to FIG. 14). FIG. 12 is a schematic drawing illustrating the positional relationship between transmitted light 16b and scattered light 16c from the central portion of the cell in which a reaction mixture 7 in the cell is irradiated with irradiation light 16a from the left hand side. For simplicity of explanation of integration time estimation, the configuration is assumed such that each light beam width is constant in the cell and the irradiation light is incident perpendicularly to the cell wall surface. Note that the incident irradiation light beam width lcw is made smaller than the cell width cw since scattered light at a cell angle becomes stray light. Assuming that cw is the cell width, lw is the total beam width to be considered, mw is the left and right margins from the cell wall surface, and v is the cell rotation speed, an integration time t can be calculated from the following expression (1).

$$t = (cw - 2 \times mw - lw)/v \qquad (1)$$

Assuming that lcw is the beam width of irradiation light irradiating the cell, ldw is the beam width of the scattered light, Cx is the optical axis of the irradiation light located at the cell wall surface, Dx is the optical axis of the scattered light, and li is the distance between the optical axis Cx and the optical axis Dx, $1w$ can be calculated from the following expression (2).

$$lw = lcw/2 + ldw/2 + li \qquad (2)$$

Further, using a cell optical path length L and an angle $\Psi$ between the optical axis of the irradiation light and the optical axis for receiving the scattered light viewed from above the cell, li can be calculated from the following expression (3).

$$li = L/2 \times \tan \Psi \qquad (3)$$

Considering the above, a maximum angle $\Psi_0$ between the optical axis of the irradiation light and the optical axis for receiving the scattered light viewed from above the cell can be expressed by the following expression (4) using expressions (1), (2), and (3).

$$\Psi_0 = \arctan((2cw - 2vt - 4mw - lcw - ldw)/L) \qquad (4)$$

As long as the angle $\Psi$ between the optical axis of the irradiation light and the optical axis for receiving the scattered light is equal to or less than $\Psi_0$ satisfying the expression (4), light can be received at a plurality of angles against reduction in cell width.

In practice, an integration time of 2 msec or more, an irradiation light beam width lcw of 0.5 mm, and a scattered light beam width ldw of 0.5 mm need to be secured depending on the amount of scattered light. Further, considering that the cell suffers from uneven formation and curved surface at corners, a left and right margin mw of about 0.5 mm is required. Furthermore, an optical path length L of 5 mm is substantially standard for transmitted light measurement. With a recent reduction in cell width, the cell width cw is equal to or less than 2.5 mm and the cell rotation speed v is approximately 100 mm/sec or more. Thus, $\Psi_0$ can be approximated to 17.7° from the expression (4).

Figure 13:
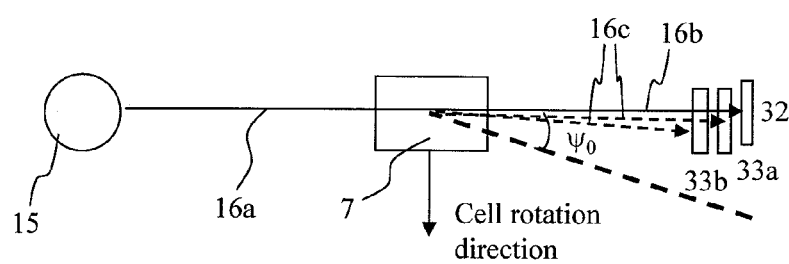
FIG. 13 is a schematic drawing of a scattered light measuring unit according to the present invention viewed from a direction perpendicular to a rotating plane of a cell disk.

FIG. 13 illustrates a cell viewed from above indicating the relationship between the transmitted light 16$b$ and the scattered light 16$c$ viewed from the direction perpendicular to a rotating plane of the cell disk. From above, when scattered light at a plurality of scattering angles is obtained, each scattered light receiver is arranged such that the angle between the transmitted light 16$b$ and the scattered light 16$c$ viewed from above is equal to or less than $\pm\Psi_0$. Thereby, the scattered light at a plurality of angles can be easily obtained while securing the integration time. Note that a plurality of scattered light receivers are respectively configured to receive light transmitted through the same wall surface as the cell wall surface through which the transmitted light passes. In order to improve the sensitivity at scattered light measurement, it is essential to reduce the receiving of scattered light occurring on the cell wall surface as much as possible. Accordingly, the cell wall surface needs to be optically flat with less surface asperities. However, the cells are manufactured by injection molding and hence an increase in optically flat surfaces leads to an increase in manufacturing costs. The surface through which the transmitted light passes has already been made an optically flat surface for measuring the amount of transmitted light. In light of this, the scattered light passing through the same wall surface as that through which the transmitted light passes can be measured without increasing the costs for cell formation.

Note that it is understood from FIGS. 10 and 11 that an appropriate reagent particle size differs depending on the angle for measuring the scattered light. For example, in the case of a measurement system for receiving the scattered light in the direction of an angle of 40°, measurement can be made with high sensitivity by setting the reagent particle size to 0.8 to 1.0 µm; and in the case of a measurement system for receiving the scattered light in the direction of an angle of 20°, measurement can be made with high sensitivity by setting the reagent particle size to 0.6 µm or less.

Figure 14:
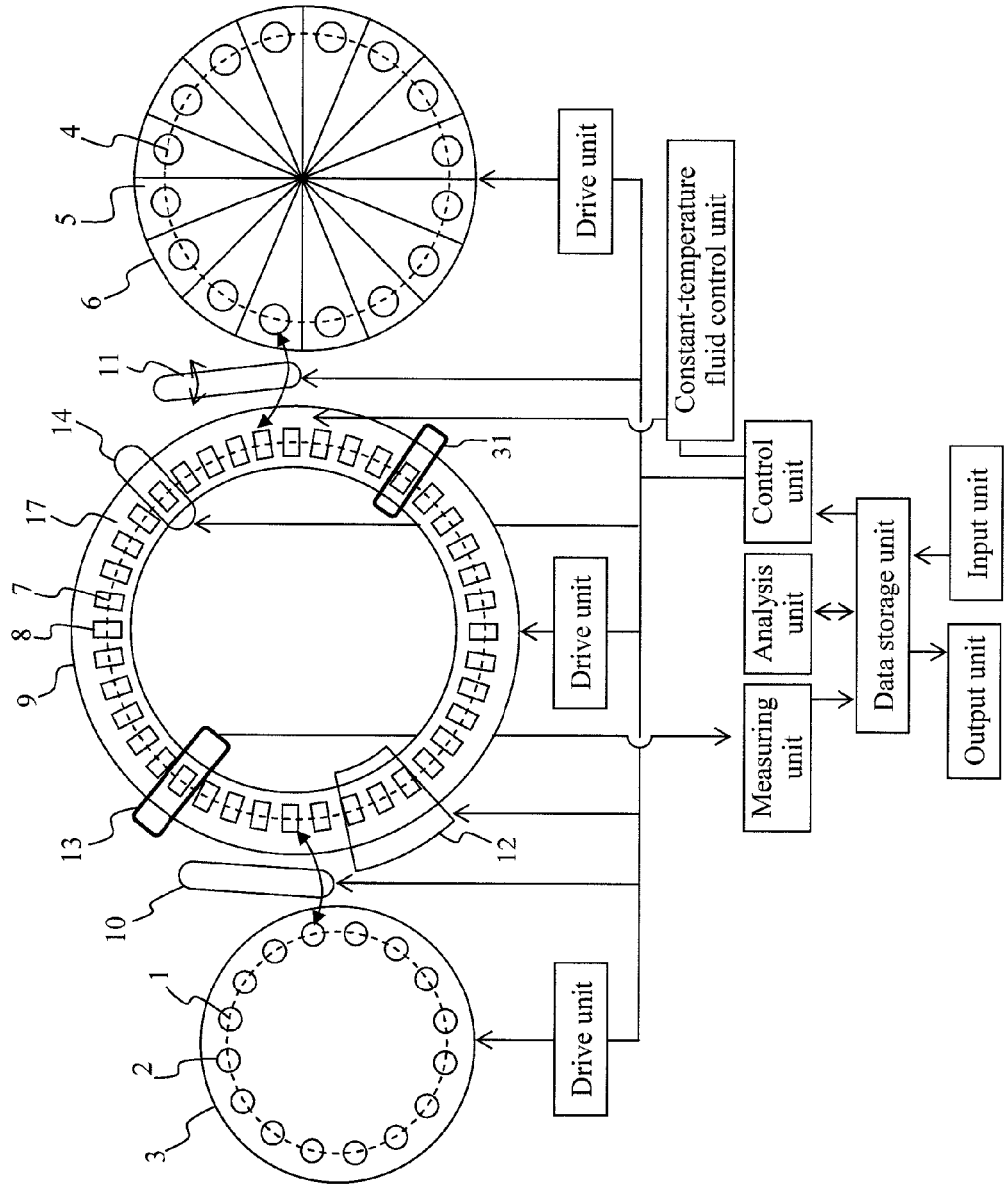
FIG. 14 is a schematic drawing illustrating an entire configuration example of an automatic analyzer according to the present invention.

Next, an example of the automatic analyzer according to the present invention will be described. FIG. 14 is a schematic drawing illustrating an entire configuration example of the automatic analyzer according to the present invention. This automatic analyzer includes a scattered light measuring unit for increasing sensitivity. The automatic analyzer mainly includes three types of disks: a sample disk 3, a reagent disk 6, and a cell disk 9, a pipetting mechanism for moving a sample and a reagent between the disks, a control unit for controlling the disks, a measuring unit, an analysis unit for processing the measured data, a data storage unit for storing the control data, the measured data, and the analyzed data, an input unit and an output unit for inputting and outputting data from and to the data storage unit.

The sample disk 3 has a plurality of sample cups 2 holding a sample 1 on a circumference thereof. The reagent disk 6 has a plurality of reagent bottles 5 holding a reagent 4. The cell disk 9 has a plurality of cells 8 on a circumference thereof. Each cell 8 holds a reaction mixture 7 made by mixing the sample 1 and the reagent 4 thereinside. The sample pipetting mechanism 10 moves a constant amount of sample 1 from the sample cup 2 to the cell 8. The reagent pipetting mechanism 11 moves a constant amount of reagent 4 from the reagent bottle 5 to the cell 8. The stirring unit 12 stirs and mixes the sample 1 and the reagent 4 in the cell 8. When the analysis is completed, the cleaning unit 14 discharges the reaction mixture 7 from the cell 8 and cleans the cell 8. The cleaned cell 8 receives another sample 1 from the sample pipetting mechanism 10 again and a new reagent 4 is received from the reagent pipetting mechanism 11 to be used for another reaction. The cell 8 is immersed in a constant-temperature fluid 17 in a constant-temperature bath in which the temperature and the flow rate are controlled. The cell 8 is moved in a state in which the cell 8 and the reaction mixture 7 therein are maintained at a constant temperature. Water is used as the constant-temperature fluid 17. The constant-temperature fluid control unit controls the temperature and the flow rate to maintain the constant-temperature fluid. The temperature is adjusted to 37±0.1° C. as the reaction temperature. The transmitted light measuring unit 13 and the scattered light measuring unit 31 are installed on a part of the circumference of the cell disk.

Figure 15:
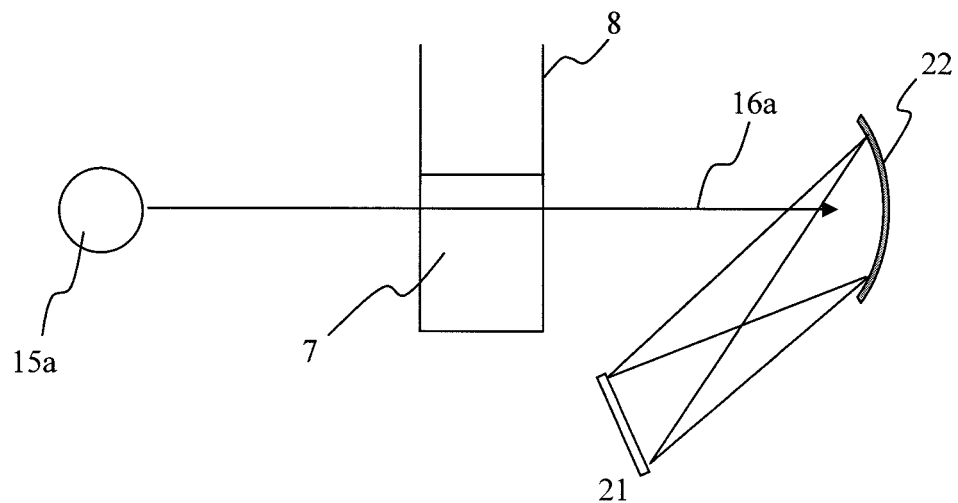
FIG. 15 is an explanatory drawing of the transmitted light measuring unit.

As illustrated in FIG. 15, the transmitted light measuring unit 13 irradiates the cell 8 with light from a halogen lamp light source 15$a$. The transmitted light beam 16$a$ is divided by a diffraction grating 22 and received by a photodiode array 21 having photodiodes arranged in an array. The wavelength of the received light are 340 nm, 405 nm, 450 nm, 480 nm, 505 nm, 546 nm, 570 nm, 600 nm, 660 nm, 700 nm, 750 nm, and 800 nm.

Figure 16:
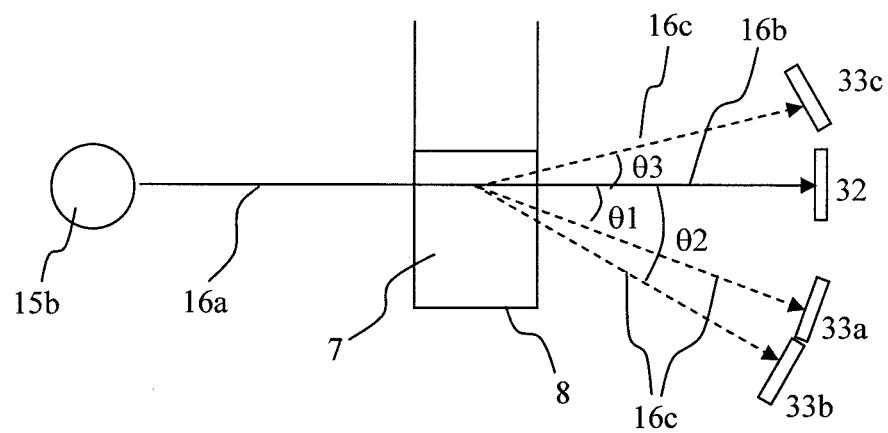
FIG. 16 is a schematic drawing of the scattered light measuring unit according to the present invention.

As illustrated in FIG. 16, the scattered light measuring unit 31 irradiated the cell 8 with irradiation light 16$a$ from an LED light source 15$b$. The transmitted light 16$b$ was received by a transmitted light receiver 32 as the monitor. The scattered light beams 16$c$ were measured by scattered light receivers 33$a$ and 33$b$. The scattered light receivers 33$a$ and 33$b$ were arranged at scattered light receiving angles θ1 and θ2, which are 20° and 40° respectively. As the LED light source 15$b$, L660-02V with an irradiation light wavelength of 660 nm manufactured by Epitex Incorporation was used. According to the present configuration, the scattered light receivers were arranged at angles of 20° and 40°, but optical systems such as a fiber and lens may be arranged in the same place so as to guide light to the scattered light receivers arranged in other places. Further, the scattered light receivers 33$a$ and 33$b$ were arranged in positions for receiving scattered light scattered downward relative to the irradiation light 16$a$, but may be arranged in positions for receiving scattered light scattered at an angle θ3 upward relative to the irradiation light 16$a$ such as the scattered light receiver 33$c$.

The angles of the optical axis of the scattered light was adjusted by monitoring the amount of light of the scattered light receiver 33$a$ on the downward side and the scattered light receiver 33$c$ on the upward side. More specifically, another scatterer was arranged at the position of the reaction mixture 7 and the scattered light receiver 33$c$ was adjusted at an angle of 20° on the upward side by matching the amount of light between the scattered light receiver 33$a$ and the scattered light receiver 33$c$. This facilitates the angle adjustment. When the scattered light receivers 33$a$, 33$b$, and 33$c$ and the transmitted light receiver 32 are configured to have the same angle as the angle θ1 on the downward side and the angle θ3 on the upward side as a single integrated unit, the positional adjustment of the transmitted light receiver 32 and like and the positional adjustment of the entire unit can be made by matching the amount of light between the scattered light receiver 33$a$ and the scattered light receiver 33$c$, which is more advantageous for reducing the adjustment time than the individual positional adjustment of each light receiver. If only the angle of 20° on the upward side is used, noise due to the positional change in the light source is measured, but the positional change in the light source can be cancelled by measuring the two positions at the angle of 20° on the upward side and on the downward side, thereby increasing sensitivity.

An LED was used as the light source 15b, but a laser, a xenon lamp, or a halogen lamp may be used. The cell had a cell width of 2.5 mm and an optical path length of 5 mm, the beam width was 0.5 mm for both the irradiation light and the scattered light, and the cell rotation speed was 200 mm/sec to secure an integration time of 5 msec.

The angle $\Psi$ between the optical axis of the irradiation light and the optical axis for receiving the scattered light viewed from above the cell was equal to or less than 17.7° considering an error in mounting precision. Thereby, light can be received at a plurality of scattering angles while securing at least 2 msec or more as the integration time. The present example secured 5 msec. Even if the cell size decreases extremely, any latex reagent of various particle sizes can be handled and a sufficient integration time can be secured by arranging a scattered light receiver on a plane perpendicular to the direction of cell rotation, namely, by arranging a scattered light receiver in a plane perpendicular to the direction of cell movement by cell disk rotation.

The analysis of the amount of constituent in the sample 1 is performed in the following procedure. First, the sample pipetting mechanism 10 dispenses a constant amount of sample 1 in the sample cup 2 into the cell 8. Next, the reagent pipetting mechanism 11 dispenses a constant amount of reagent 4 in the reagent bottle 5 into the cell 8. When dispensed, the sample disk 3, the reagent disk 6, and the cell disk 9 are rotatably driven by the respective drive units under the control of the control unit to move the sample cup 2, the reagent bottle 5, and the cell 8 with the timing of the pipetting mechanism. Then, the stirring unit 12 stirs the sample 1 and the reagent 4 in the cell 8 to make the reaction mixture 7. Note that FIG. 14 is a simplified drawing illustrating only one reagent disk and reagent pipetting mechanism, but typically two reagent disks, reagent pipetting mechanisms, and stirring units are used.

Each time the light passes through the measurement positions of the transmitted light measuring unit 13 and the scattered light measuring unit 31 while the cell disk 9 is rotating, the transmitted light and the scattered light of the reaction mixture 7 are measured and sequentially accumulated as reaction process data in the data storage unit through the measuring unit. After the optical measurement for about 10 minutes, the cleaning mechanism 14 cleans the inside of the cell 8 and then the process moves on to the next analysis. During the period, if necessary, the reagent pipetting mechanism 11 adds another reagent 4 to the cell 8 for pipetting, and the stirring unit 12 stirs the reagent 4 to be further measured for a specific time. Thus, the reaction process data of the reaction mixture 7 is stored in the data storage unit at a specific time interval. The analysis unit analyzes the accumulated reaction process data to determine the amount of constituent based on the calibration curve data for each test item. The data required for each unit to control and analyze is inputted from the input unit to the data storage unit. The calibration curve data is maintained in the data storage unit. The output unit outputs various data, results, and alarms through a display or the like.

Figure 17:
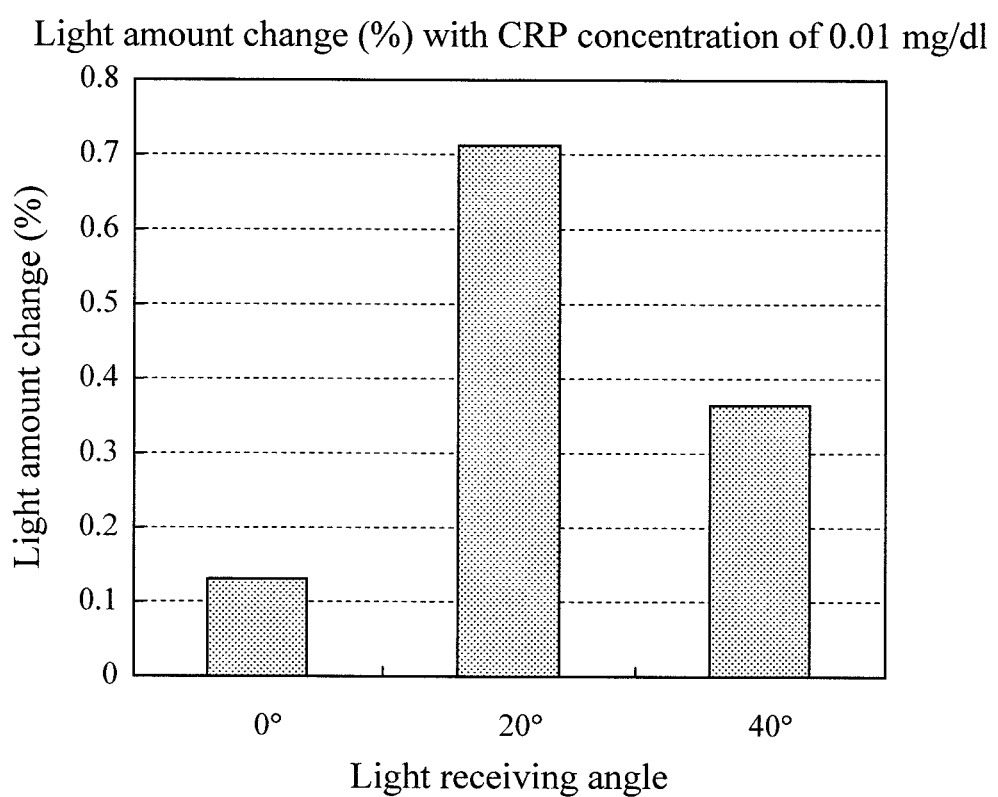
FIG. 17 is a graph illustrating an experimental result of angular dependence of the ratio of change in the amount of scattered light due to latex agglutination.

FIG. 17 illustrates the experimental results of the angular dependence of the ratio of change in scattered light for the latex agglutination reaction according to the present example. The CRP reagent (Nanopia CRP manufactured by Sekisui Chemical Co., Ltd.) was used as the reagent, and the CRP Calibrator (manufactured by Sekisui Chemical Co., Ltd.) was diluted and used as the sample. The light amount change (%) in the amount of transmitted light in the direction of an angle of 0° with a concentration of 0.01 mg/dL was 0.13%, and the light amount change (%) in the direction of an angle of 20° was 0.71%, which means that five or more times the light amount change (%) was detected and it was confirmed that the detection was made with increased sensitivity.

REFERENCE SIGNS LIST 1 sample
2 sample cup
3 sample disk
4 reagent
5 reagent bottle
6 reagent disk
7 reaction mixture
8 cell
9 cell disk
10 sample pipetting mechanism
11 reagent pipetting mechanism
12 stirring unit
13 transmitted light measuring unit
14 cleaning unit
15 light source
15a halogen lamp
15b LED
16 light
16a irradiation light
16b transmitted light
16c scattered light
17 constant-temperature fluid
21 photodiode array
22 diffraction grating
31 scattered light measuring unit
32 transmitted light receiver
33a, 33b, 33c scattered light receiver

The invention claimed is:

1. An automatic analyzer comprising:
a cell disk having a cell disposed on a circumference of the cell disk, the cell configured to hold a reaction mixture of a sample and a reagent mixed with each other inside the cell, and the cell disk configured to repeatedly rotate and terminate rotation; and
a scattered light measuring unit including a light source and a plurality of light receivers, the scattered light measuring unit configured to irradiate the cell with irradiation light from the light source during rotation of the cell disk, and configured to measure, by using at least one of the plurality of light receivers, light scattered by the reaction mixture in the cell;
wherein the plurality of light receivers are arranged in a plane perpendicular to the direction of movement of the cell caused by the rotation of the cell disk; and
wherein the scattered light measuring unit is configured to receive the scattered light at each of a plurality of different scattering angles.

2. The automatic analyzer according to claim 1, wherein when viewed from a direction perpendicular to a rotating plane of the cell disk, the angle between the optical axis of the irradiation light and the optical axis of the scattered light received by the plurality of light receivers is within a range of ±17.7°.

3. The automatic analyzer according to claim 1, wherein the plurality of light receivers receive the scattered light passing through the same cell wall as the cell wall through which the transmitted light passes.

4. The automatic analyzer according to claim 1, wherein at least one of the plurality of light receivers receives the scattered light between ta dark ring and a subsequent bright ring.

5. The automatic analyzer according to claim 4, wherein the dark ring and the bright ring correspond to a first dark ring and a first bright ring, respectively.

6. The automatic analyzer according to claim 1, wherein of the plurality of light receivers, the first light receiver is arranged at a position for receiving the scattered light at a scattering angle of 30° or less, and the second light receiver is arranged at a position for receiving the scattered light at a scattering angle of 30° to 50°.

7. An automatic analyzer comprising:
- a cell disk having a cell disposed on a circumference of the cell disk, the cell configured to hold a reaction mixture of a sample and a reagent mixed with each other inside the cell, and the cell disk configured to repeatedly rotate and terminate rotation;
- a scattered light measuring unit including a light source, a first light receiver, and a second light receiver, the scattered light measuring unit configured to irradiate the cell with irradiation light from the light source during rotation of the cell disk, and configured to measure, by receiving scattered light by using the first light receiver and the second light receiver, light scattered by the reaction mixture in the cell;
- wherein the second light receiver is arranged above the first light receiver, in a direction perpendicular to a rotating plane of the cell disk; and
- wherein each of the first light receiver and the second light receiver receive the scattered light at a different scattering angle.

8. An automatic analyzer comprising:
- a cell disk having a cell disposed on a circumference of the cell disk, the cell configured to hold a reaction mixture of a sample and a reagent mixed with each other inside the cell, and the cell disk configured to repeatedly rotate and terminate rotation; and
- a scattered light measuring unit including a light source and a plurality of light receivers, the scattered light measuring unit configured to irradiate the cell with irradiation light from the light source during rotation of the cell disk, and configured to measure, by receiving scattered light by using the plurality of light receivers, light scattered by the reaction mixture in the cell;
- wherein the plurality of light receivers are arranged in a direction perpendicular to a rotating plane of the cell disk; and
- wherein each of the plurality of light receivers receives scattered light at a different scattering angle.

* * * * *